United States Patent
Tanimoto

(10) Patent No.: US 7,629,565 B2
(45) Date of Patent: Dec. 8, 2009

(54) IMAGING APPARATUS CAPABLE OF CAPTURING A SYNTHESIZED IMAGE OF A VISIBLE-SPECTRUM IMAGE AND AN INFRARED-SPECTRUM IMAGE

(75) Inventor: Takashi Tanimoto, Motosu-gun (JP)

(73) Assignees: Sanyo Electric Co., Ltd., Moriguchi (JP); Sanyo Semiconductor Co., Ltd., Ora (JP)

( * ) Notice: Subject to any disclaimer, the term of this patent is extended or adjusted under 35 U.S.C. 154(b) by 0 days.

(21) Appl. No.: 12/230,743

(22) Filed: Sep. 4, 2008

(65) Prior Publication Data

US 2009/0065679 A1   Mar. 12, 2009

(30) Foreign Application Priority Data

Sep. 12, 2007   (JP)   ............... 2007-236636

(51) Int. Cl.
   *H01L 27/00*   (2006.01)
(52) U.S. Cl. .................... 250/208.1; 250/226
(58) Field of Classification Search .............. 250/208.1, 250/226; 600/181
   See application file for complete search history.

(56) References Cited

U.S. PATENT DOCUMENTS

| | | | | |
|---|---|---|---|---|
| 5,891,016 | A | * | 4/1999 | Utsui et al. .................. 600/181 |
| 6,293,911 | B1 | * | 9/2001 | Imaizumi et al. ............ 600/160 |
| 6,716,162 | B2 | * | 4/2004 | Hakamata .................... 600/181 |
| 2005/0133690 | A1 | | 6/2005 | Higashitsutsumi |
| 2008/0039696 | A1 | * | 2/2008 | Kamihara .................... 600/181 |

FOREIGN PATENT DOCUMENTS

| | | |
|---|---|---|
| JP | A-2005-184690 | 7/2005 |
| JP | A-2005-261974 | 9/2005 |

\* cited by examiner

*Primary Examiner*—John R Lee
(74) *Attorney, Agent, or Firm*—Oliff & Berridge, PLC

(57) ABSTRACT

An imaging apparatus for capturing a synthesized image of a visible-spectrum image and an infrared-spectrum image implements a proper synthesis balance without amplification of the signal of the infrared-spectrum image obtained by a solid-state image sensor or attenuating the visible light incident on the image sensor. A visible light source (20) and an excitation light source (22) are provided separately. The visible-spectrum image and the infrared-spectrum image, which is based on infrared fluorescent light emitted from a fluorescent substance in response to excitation light, are captured separately by a single image sensor (12) using staggered exposure periods. A signal-processing circuit (16) synthesizes the two images. The synthesis balance is adjusted by the exposure time or the respective illumination intensities of the two light sources.

2 Claims, 4 Drawing Sheets

IMAGING APPARATUS CAPABLE OF CAPTURING A SYNTHESIZED IMAGE OF A VISIBLE-SPECTRUM IMAGE AND AN INFRARED-SPECTRUM IMAGE

CROSS-REFERENCE TO RELATED APPLICATION

The priority application number JP2007-236636 upon which this patent application is based is hereby incorporated by reference.

BACKGROUND OF THE INVENTION

1. Field of the Invention

The present invention relates to an imaging apparatus that is capable of capturing a synthesized image of a visible-spectrum image and an infrared-spectrum image resulting from an infrared-fluorescing substance.

2. Description of the Related Art

Fluorescent materials are used in technology for detecting the presence of specific materials or structures that are indefinite in visible-spectrum images of an object. Indocyanine green ("ICG" hereinbelow) is an example of a fluorescent material. ICG is a dye that absorbs and is excited by near-infrared light of approximately 800 nm, and fluoresces near-infrared light of approximately 850 nm. This dye can be administered to the human body as a contrast medium, and the infrared-spectrum image that is thereby observed is used during surgery, disease diagnosis, and other applications. The endoscope apparatus in, e.g., Japanese Laid-open Patent Application No. 2005-261974, can capture visible-spectrum images of the interior of body cavities and can also emit excitation light onto the subject and capture fluorescent images of the interior of body cavities of a person to whom ICG has been administered.

Japanese Laid-open Patent Application No. 2005-184690 discloses a color imaging device in which visible-spectrum pixels that are sensitive to the visible-spectrum components of red (R), green (G), and blue (B), and infrared-spectrum pixels that are essentially only sensitive to infrared-spectrum components are combined into a two-dimensional array. According to this solid-state imaging device, the signal of the infrared-spectrum pixels is used to remove offsets due to infrared-spectrum components from the signal of the visible-spectrum pixels, and a visible-spectrum image having improved color reproducibility is obtained. This solid-state imaging device can also simultaneously capture visible-spectrum images and infrared-spectrum images.

Images synthesized from normal images, which are obtained as visible-spectrum images, and infrared-spectrum images, which are based on fluorescent light, are useful for diagnosis, surgery, and other applications. The intensity of fluorescent light is usually fainter than visible light. Conventional imaging apparatuses therefore amplify the signal of the infrared-spectrum image in the solid-state imaging device and the signal-processing circuit and use a filter to attenuate the visible light incident on the solid-state imaging device, whereby the intensity balance of the visible-spectrum image and the infrared-spectrum image that are synthesized are adjusted.

However, problems have been presented in that noise increases and image quality readily deteriorates when amplifying the signal of the infrared-spectrum image in the solid-state imaging device and the signal-processing circuit, and using a filter to attenuate the visible light incident on the solid-state imaging device in order to implement a proper synthesis balance. Problems are therefore presented in that obtaining proper synthesized images from visible-spectrum images and infrared-spectrum images is difficult.

SUMMARY OF THE INVENTION

The present invention was devised in order to solve the aforedescribed problems, and it is an object thereof to provide an imaging apparatus capable of obtaining a proper synthesized image of a visible-spectrum image and an infrared-spectrum image.

An imaging apparatus according to the present invention comprises a first light source for irradiating a subject with a first component light of a visible-spectrum band; a second light source for irradiating the subject with a second component light of a wavelength for exciting a predetermined infrared-fluorescing substance for emitting infrared fluorescent light; an optical filter for transmitting the infrared fluorescent light and a spectrum component corresponding to the first component light and for preventing the transmission of a band component corresponding to the second component light from among light from the subject; a solid-state imaging device capable of capturing a visible-spectrum image and an infrared-spectrum image on the basis of light transmitted through the optical filter; a control part for illuminating the first light source and the second light source in alternation and for causing the solid-state imaging device to capture an image when each of the first light source and the second light source is illuminated; and an image signal-processing part for generating a synthesized image signal representing a synthesized image based on the visible-spectrum image captured as a result of the first light source being illuminated and on the infrared-spectrum image captured as a result of the second light source being illuminated.

DESCRIPTION OF THE PREFERRED EMBODIMENTS

Embodiments of the present invention will be described below on the basis of the drawings.

Figure 1:
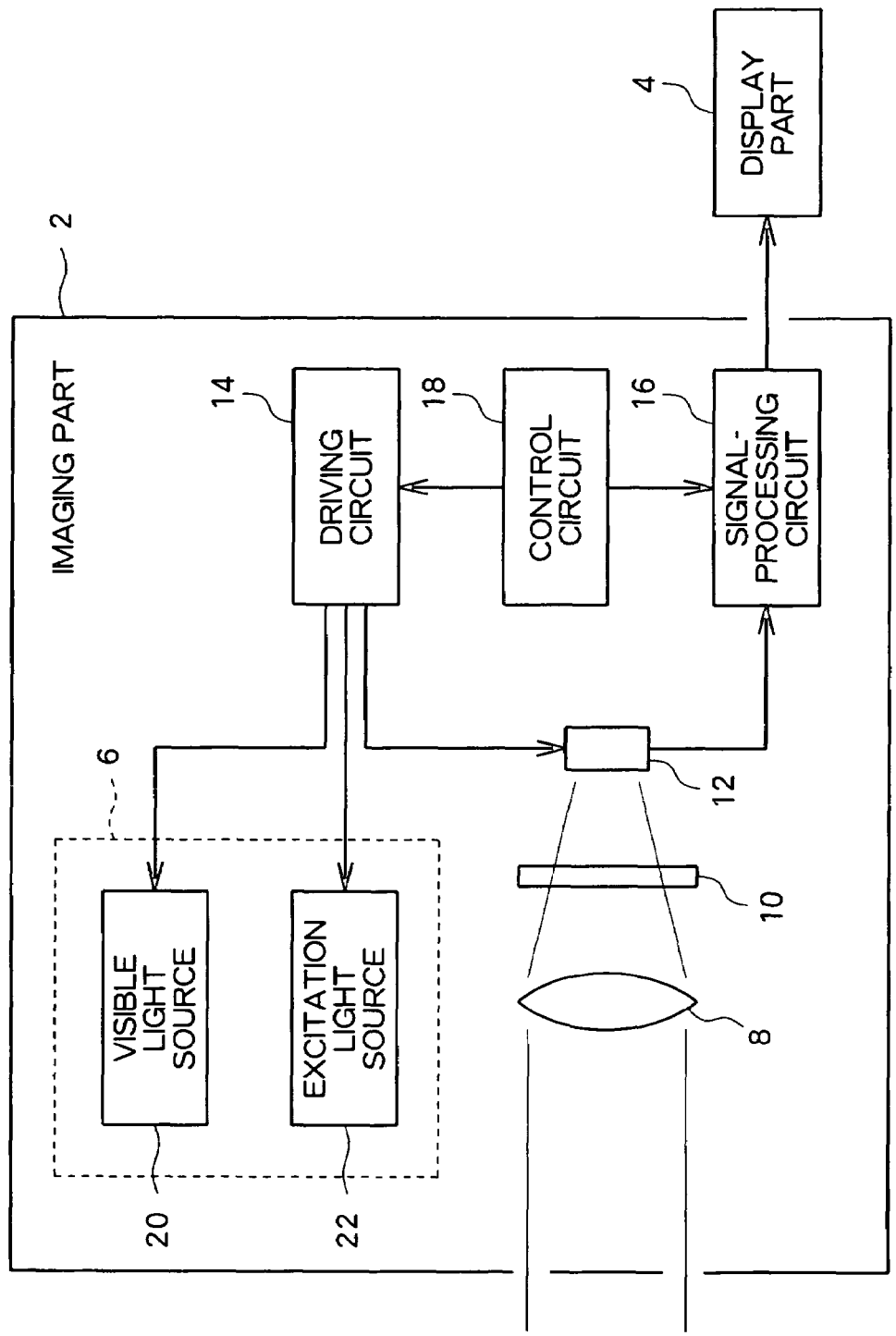
FIG. 1 is a block diagram that shows a schematic structure of an imaging apparatus according to an embodiment of the present invention.

The present embodiment is an endoscopic imaging apparatus for capturing a synthesized image of an infrared-spectrum image and a visible-spectrum image from a subject, e.g., a human body wherein ICG has been injected into the blood vessels as a fluorescent contrast medium. FIG. 1 is a block diagram that shows a schematic structure of the imaging apparatus according to the present embodiment. The present imaging apparatus is divided into, e.g., an imaging part 2 and a display part 4. The imaging part 2 comprises a light source 6, an optical system 8, an optical filter 10, a CCD image sensor 12, a driving circuit 14, a signal-processing circuit 16, and a control circuit 18. The imaging part 2 is provided to the distal part of the endoscope. In order to make the distal part as small as possible and alleviate the burden on the person, only a portion of the imaging part 2, e.g., the light source 6, the optical system 8, the optical filter 10, and the CCD image sensor 12, may be housed in the distal part, and the other portion may be provided to a unit outside the body cavity. In this instance, the light source 6 and the CCD image sensor 12, which are within the distal part, and the unit outside the body cavity are connected by a signal line that passes within a cable-shaped inserting part of the endoscope. The light source 6 can also be configured so that light produced by a light-emitting part provided outside the body cavity is guided to the distal part via an optical fiber or the like. The display part 4 is placed outside the body cavity and displays an image of the interior of the body cavity to a doctor or others.

The light source 6 is composed of a visible light source 20 and an excitation light source 22. The visible light source emits visible light over a relatively wide band that includes R (red), G (green), and B (blue), and the excitation light source emits light over a relatively narrow band that includes the excitation wavelength of ICG. In the present imaging apparatus, the capture of visible-spectrum image and infrared-spectrum image is performed by the CCD image sensor 12 in a time-divided manner. The visible light source 20 and the excitation light source 22 can accordingly be made to illuminate separately. A xenon lamp, a white LED (light emitting diode), or the like may be used as the visible light source 20. The excitation light source 22 may be, e.g., an LED or other light-emitting semiconductor device having a peak wavelength of 780 nm, in accordance with the excitation wavelength of ICG. In particular, GaAs and other laser diodes (LD) are used in reading compact discs (CDs), and these devices can also be employed as the device for emitting 780-nm light in the present apparatus.

In order to sharply image the fluorescent light emitted by ICG, light components near the fluorescent wavelength other than the fluorescent light from ICG are preferably minimal. Capture of the fluorescent infrared-spectrum image is therefore performed so that only the excitation light source 22 is on, and the visible light source 20 is off, as described hereinafter. Other light sources are essentially not present inside the body cavity, and thus capture of the infrared-spectrum image from the fluorescent light of ICG can be properly performed by turning off the visible light source 20.

The light from the subject is taken into the present imaging apparatus via the optical system 8. The optical system 8 is composed of a lens or the like and forms an optical image on the imaging area of the CCD image sensor 12.

Figure 2:
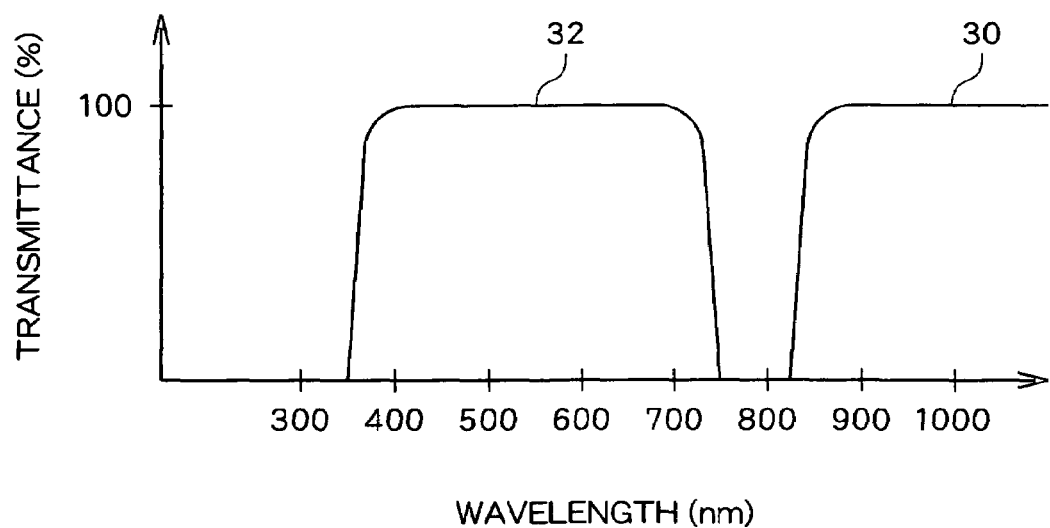
FIG. 2 is a schematic diagram that shows the spectral transmission characteristics of the optical filter.

The optical filter 10 is positioned on the path of light incident on the CCD image sensor 12. FIG. 2 is a schematic diagram that shows the spectral transmission characteristics of the optical filter 10. The optical filter 10 has a characteristic 30 for properly allowing the transmission of bands near 850 nm, which is the fluorescence wavelength, while the optical filter 10 blocks the transmission of light in bands near 780 nm, which is the excitation wavelength, properly. The CCD image sensor 12 can thereby prevent the capture of unnecessary images due to excitation light reflected by the subject and can properly capture an infrared-spectrum image from the fluorescent light. The optical filter 10 also has a characteristic 32 for transmitting visible light. The characteristics of the optical filter 10 described herein can be implemented by, e.g., forming a thin film in which approximately 10 to 60 layers of silica/titania or the like are laid by repeated vacuum deposition.

In the present imaging apparatus, the desired synthesis balance between the visible-spectrum image and the infrared-spectrum image in the synthesized image can be adjusted using the exposure conditions of the visible-spectrum image and the infrared-spectrum image, which are taken separately, i.e., using the respective exposure times of the visible-spectrum image and the infrared-spectrum image and the respective illumination intensities of the visible light source 20 and the excitation light source 22. In other words, adjusting the balance of transmittance between the visible spectrum band the infrared spectrum band of the optical filter 10 is essentially unnecessary for implementing the desired synthesis balance. The optical filter 10 used in the present embodiment can therefore have a high transmittance of, e.g., 100% for the transmission characteristics 30, 32 in both bands. The transmittances of the characteristics 30, 32 of the optical filter 10 may also be different. The present imaging apparatus can essentially implement a proper synthesis balance by adjusting the exposure conditions of the visible-spectrum image and the infrared-spectrum image even when differences exist in the transmittances of the optical filter 10. Put another way, variation in the transmittances of the characteristics 30, 32 of the optical filter 10 in the present imaging apparatus can be readily absorbed by adjusting the exposure conditions. Accuracy requirements for the optical filter 10 are therefore relaxed, and the manufacture or selection of the optical filter 10 is facilitated.

Figure 3:
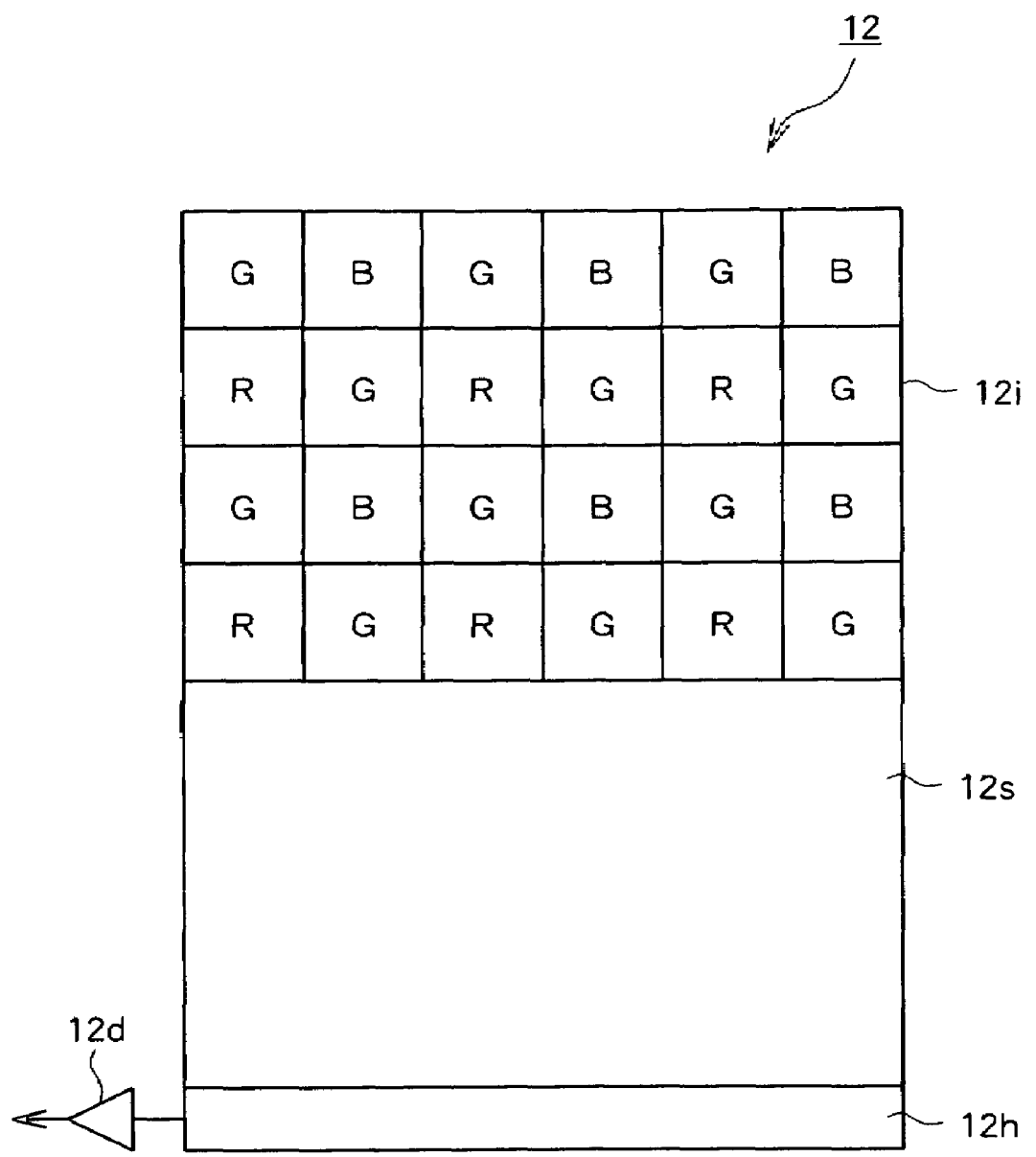
FIG. 3 is a schematic plan view that shows a schematic structure of the CCD image sensor.

The CCD image sensor 12 operates on the basis of various clock signals from the driving circuit 14 and generates an image signal corresponding to the subject. FIG. 3 is a schematic plan view that shows a schematic structure of the CCD image sensor 12. The CCD image sensor 12 shown in FIG. 3 is of the frame-transfer type and is composed of an imaging part 12*i*, a storage part 12*s*, a horizontal transfer part 12*h*, and an output part 12*d*, which are formed on a semiconductor substrate.

Each bit of the vertical shift registers that constitute the imaging part 12*i* corresponds to a respective pixel and functions as a light-receiving pixel. A color filter is positioned for each of the light-receiving pixels, and the light component to which the light-receiving pixel is sensitive is set according to the transmission characteristics of that color filter. A Bayer color-filter array is positioned in the imaging part 12*i*.

Figure 4:
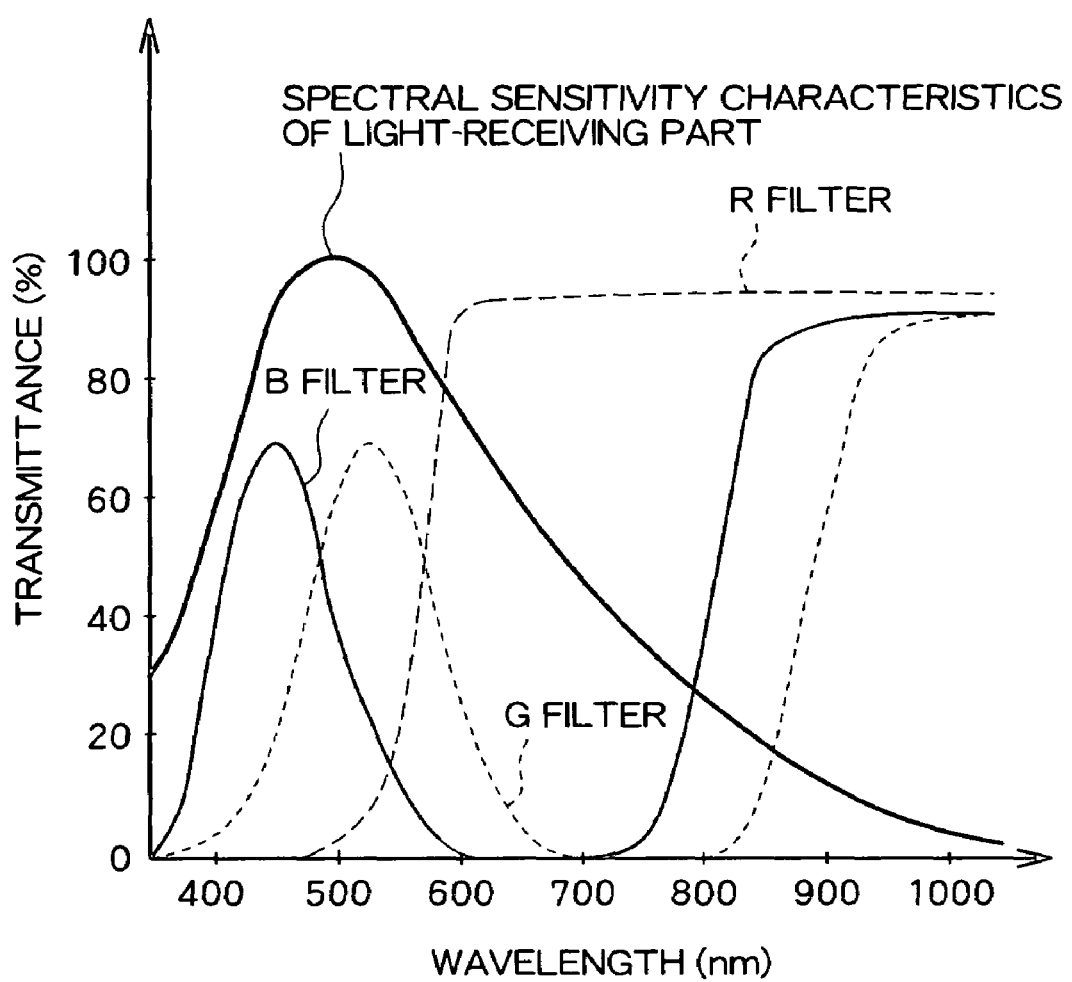
FIG. 4 is a graph that shows the spectral transmission characteristics of each of the RGB filters and the spectral sensitivity characteristics of the photodiode.

The color filters are formed using, e.g., colored organic materials. The color filters transmit visible light corresponding to the respective colors of the filters, but these materials also transmit infrared light. FIG. 4 is a schematic example graph that shows the spectral transmission characteristics of each of the RBG filters. FIG. 4 also shows the spectral sensitivity characteristics of the photodiode. The transmittances of the filters of each color display inherent spectral characteristics in the visible spectrum according to the respective color, but the spectral characteristics in the infrared spectrum are all similar.

On the other hand, the photodiode is sensitive to wavelengths longer than 780 nm in the near-infrared spectrum in addition to being sensitive to wavelengths in the entire visible spectrum up to approximately 780 nm. When an infrared-spectrum component impinges on a light-receiving pixel, the infrared-spectrum component is transmitted through the color filter and produces a signal charge in the photodiode. A signal charge corresponding to a visible-spectrum component according to the color of the filter positioned on the pixel and a signal charge corresponding to an infrared-spectrum component included in the incident light can be accumulated in each of the light-receiving pixels.

The signal charges produced in each of the light-receiving pixels of the imaging part 12*i* are transferred to the output part 12*d* via the storage part 12*s* and the horizontal transfer part 12*h*. The output part 12*d* is composed of an electrically isolated capacitance and an amp for extracting changes in the electric potential of the capacitance. The output part receives the signal charges output from the horizontal transfer part 12*h* into the capacitance in one-bit units. The information charges are converted to voltage values and output as time-series image signals.

The driving circuit 14 receives a timing-control signal or the like from the control circuit 18, generates the various clock signals for driving the CCD image sensor 12, and supplies these signals to the CCD image sensor 12. The driving circuit 14 also receives instructions from the control circuit 18 and, e.g., controls the on and off states of the visible light source 20 and the excitation light source 22 in concert with the imaging operation of the CCD image sensor 12. Specifically, when capturing the visible-spectrum image, the visible light source 20 is on and the excitation light source 22 is off. When capturing the infrared-spectrum image, the excitation light source 22 is on, and the visible light source 20 is off.

The signal-processing circuit 16 generates an image signal that represents the synthesized image resulting from synthesizing the visible-spectrum image and the infrared-spectrum image on the basis of the respective image signals of the visible-spectrum image and the infrared-spectrum image captured and output by the CCD image sensor 12 in a time-divided manner. The signal-processing circuit 16 includes an analog signal processing circuit, and A/D converter circuit, and a digital signal processing circuit.

The analog signal processing circuit performs processes such as amplification and sample-and-hold on the analog image signal output from the output part 12*d*. The A/D converter circuit uses a predetermined quantization bit rate to digitize the image signal output from the analog signal processing circuit. The signal is converted into image data, and this data is output.

The digital signal processing circuit receives the image data from the A/D converter circuit and performs various processes. The digital signal processing circuit performs contour correction, gamma correction, and the like separately on the visible-spectrum image and the infrared-spectrum image. Gain, offset, and the like may also be set separately.

The digital signal processing circuit also performs predetermined processes on the visible-spectrum image and the infrared-spectrum image and generates brightness data and color data for the synthesized image resulting from overlaying these images.

The digital signal processing circuit performs, e.g., a filtering process on all of the RGB data sampled by each of the RGB light-receiving pixels for the image data captured during illumination of the visible light source 20. This filtering process comprises a spatial interpolation process that is performed on R data, G data and B data, respectively, obtained at different sampling points from each other, whereby RGB pixel values are defined at each of the sampling points that constitute the image. Processes for removing pixel defects and random noise are also performed during the filtering process. All of the RGB data is represented separately as (R), (G), and (B) after this filtering process.

In the data obtained during illumination of the excitation light source 22 for each of the light-receiving pixels, all of the light-receiving pixels constitute image data for the infrared-spectrum image regardless of the RGB type. In other words, data for infrared fluorescence is obtained at each of the sampling points corresponding to the respective light-receiving pixels even when the aforedescribed spatial interpolation process that was performed for the visible-spectrum image is not performed for the infrared-spectrum image. However, the digital signal processing circuit performs processes for correcting discrepancies in the transmittance of infrared light for each type of RGB filter for each of the pixel values. The digital signal processing circuit performs this correction, e.g., in the same manner as the white-balance adjustment on the visible-spectrum image. Specifically, the average of the pixel values for the R light-receiving pixels, the average of the pixel values for the G light-receiving pixels, and the average of the pixel values for the B light-receiving pixels are determined for the image data of the infrared-spectrum image, and correction coefficients are designated for R, G, and B so that the averages are equivalent. The digital signal processing circuit makes use of the correction coefficients corresponding to the RGB types of the light-receiving pixels and calculates corrected pixel values for the pixel values of each of the light-receiving pixels. The image data of the infrared-spectrum image are represented as (IR) after this correction process.

The digital signal processing circuit uses (R), (G), (B), and (IR) to perform a process for generating an image signal representing the synthesized image, and generates color-difference data (color-difference signals) Cr, Cb and brightness data (a brightness signal) Y for each of the sampling points. The digital signal processing circuit can also be configured to display the infrared-spectrum image as any desired color in the synthesized image.

The image signal of the synthesized image generated by the signal-processing circuit 16 is input to the display part 4, and the image is displayed on a liquid crystal display or other display device. When, e.g., ICG is injected into the blood vessels and endoscopic observation is performed, an infrared-spectrum image, in which blood vessels and the like having a high concentration of ICG stand out in white, is synthesized into a visible-spectrum image of the interior of the body cavity displayed as a color image corresponding to (R), (G), and (B), whereby a synthesized image is obtained.

Exposure control for the present imaging apparatus will be described next. The digital signal processing circuit in the signal-processing circuit 16 integrates the image data in units of single screens and outputs the integration results to the control circuit 18. The control circuit 18 controls the driving circuit 14 on the basis of the integration results. Exposure times E1, E2 of the visible-spectrum image and the infrared-spectrum image, respectively, are lengthened or shortened, and illumination intensities L1, L2 of the visible light source 20 and the excitation light source 22, respectively, are increased or decreased, whereby, e.g., feedback control is performed so that integration values A1, A2 for one screen of the image data for the visible-spectrum image and the infrared-spectrum image, respectively, are brought to the desired values (target values $\alpha_{T1}$, $\alpha_{T2}$).

The respective target values $\alpha_{T1}$, $\alpha_{T2}$ of the integration values A1, A2 can be set according to the desired synthesis balance between the visible-spectrum image and the infrared-spectrum image in the synthesized image. When, e.g., it is desired that the visible-spectrum image be displayed more clearly than the infrared-spectrum image in the synthesized image, $\alpha_{T1}$ is set to be larger than $\alpha_{T2}$, whereas when it is desired that the infrared-spectrum image be displayed more clearly than the visible-spectrum image, $\alpha_{T2}$ is set to be larger than $\alpha_{T1}$. The desired synthesis balance can thus be implemented in the present imaging apparatus essentially by adjusting the exposure time and the illumination intensity. In other words, amplification gain in the infrared-spectrum image, which is obtained on the basis of the generally faint fluorescent light, is minimized by the signal-processing circuit 16, whereby increases in noise are minimized, and improvements in the quality of synthesized image are attained.

The target values $\alpha_{T1}$, $\alpha_{T2}$ in the control circuit 18 are set by, e.g., the user. The control circuit 18 controls the driving circuit 14 and the signal-processing circuit 16 so that capture of the visible-spectrum image and the infrared-spectrum image occurs in alternation. Imaging is performed in, e.g., the following order: the visible-spectrum image P1(k) of the kth frame, the infrared-spectrum image P2(k) of the kth frame, the visible-spectrum image P1(k+1) of the (k+1)th frame, and the infrared-spectrum image P2(k+1) of the (k+1)th frame. P1(k) and P2(k) are synthesized, and a synthesized image Pc(k) of the kth frame is generated. P1(k+1) and P2(k+1) are synthesized, and a synthesized image Pc(k+1) of the (k+1)th frame is generated. In this instance, "k" is an integer.

The control circuit 18 in this instance, e.g., designates the exposure conditions of the visible-spectrum image P1(n) of the nth frame using feedback control for reducing the difference between the target value $\alpha_{T1}$ and the integration value A1(n−1) for the visible-spectrum image P1(n−1) that was captured immediately before. The control circuit 18, e.g., holds the illumination intensity L1 of the visible light source 20 constant and lengthens or shortens the exposure time E1. In other words, when A1(n−1)>$\alpha_{T1}$, the exposure time E1(n) for P1(n) is set to be shorter than E1(n−1), and when A1(n−1)<$\alpha_{T1}$, E1(n) is set to be longer than E1(n−1).

The same manner of exposure control can be performed for the infrared-spectrum image. In other words, the control circuit 18 designates the exposure conditions of the infrared-spectrum image P2(n) using feedback control for reducing the difference between the target value $\alpha_{T2}$ and the integration value A2(n−1) for the infrared-spectrum image P2(n−1). The control circuit 18, e.g., first holds the illumination intensity L2 of the excitation light source 22 constant and lengthens or shortens the exposure time E2. In other words, when A2(n−1)>$\alpha_{T2}$, the exposure time E2(n) for P2(n) is set to be shorter than E2(n−1), and when A2(n−1)<$\alpha_{T2}$, E2(n) is set to be longer than E2(n−1).

In a state in which the fluorescent light is faint, the control circuit 18 can be configured to set the illumination intensity L2 to a higher level and then lengthen or shorten the exposure time E2. Situations in which, e.g., the exposure time E2 exceeds a predetermined upper-limit value designated according to the frame rate or other parameter can thereby be avoided.

Feedback control for the visible-spectrum image can also be performed on the basis of the visible-spectrum images of a plurality of preceding frames instead of just one preceding frame. In the same manner, feedback control for the infrared-spectrum image can also be performed on the basis of the infrared-spectrum images of a plurality of preceding frames.

Another method of control using the control circuit 18 will be described next. In this method of control, exposure control for the visible-spectrum image P1(n), which is the first to be captured among the pair of images P1(n), P2(n) that constitute the synthesized image Pc(n), is performed in the same manner as the aforedescribed visible-spectrum image. In other words, e.g., the exposure time E1(n) is designated by feedback control for reducing the difference between the target value $\alpha_{T1}$ and the integration value A1 of the visible-spectrum image captured previously.

On the other hand, exposure control for the infrared-spectrum image P2(n), which is the last of the aforementioned pair of images to be captured, is performed by combining:

(1) feedback control for reducing the difference between the target value $\alpha_{T2}$ and the integration value A2 of the infrared-spectrum image captured previously; and (2) feedforward control on the integration value A1(n) of the visible-spectrum image P1(n) captured immediately before, in order to implement a target synthesis balance θ defined by the target values $\alpha_{T1}$, $\alpha_{T2}$.

The index θ(n) that represents the synthesis balance at the nth frame, and the value $\theta_T$ of the θ at the target synthesis balance are defined respectively by the following equations.

$$\theta(n) = A2(n)/A1(n)$$

$$\theta_T = \alpha_{T2}/\alpha_{T1}$$

Exposure control will be described for a case in which, e.g., the integration value A2 of the preceding infrared-spectrum image P2(n−1) is a multiple $\lambda_2$ ($\lambda_2<1$) of the target value $\alpha_{T2}$, and the integration value A1 of the immediately preceding visible-spectrum image P1(n) is a multiple $\lambda_1$ ($\lambda_1>1$) of the target value $\alpha_{T1}$.

It shall be assumed that the integration value A1 of the visible-spectrum image P1(n) that is synthesized into the infrared-spectrum image is a value $\lambda_1 \alpha_{T1}$ that is larger than the target value $\alpha_{T1}$, even though the feedback control of (1) above was performed on the basis of the integration value A2 of the previous infrared-spectrum image, and the integration value A2 for the infrared-spectrum image P2(n) was set to the target value $\alpha_{T2}$. Therefore, $\theta/\theta_T$ is $1/\lambda_1$. In other words, $\theta<\theta_T$ in this instance, and the synthesis balance is offset from the target state. Specifically, the visible-spectrum image is displayed more brightly in the synthesized image, and as a result, the infrared-spectrum image is displayed comparatively darkly and sinks into the background.

In response to these conditions, control for reducing the deviation of the integration value A2 of the previous infrared-spectrum image relative to the target value $\alpha_{T2}$ and control for changing the integration value A2 of the infrared-spectrum image P2(n) following the integration value A1 of the immediately preceding visible-spectrum image P1(n) are performed in a control system that combines the feedback control of (1) and the feedforward control of (2) according to the present invention. As a result, the exposure conditions for P2(n) are set so that A2(n) approaches the value given by the following equation.

$$(\lambda_2/\lambda_1)A2(n-1)$$

When controlling the exposure time, the control circuit 18, e.g., uses the exposure time E2(n−1) for P2(n−1) as a reference for setting the exposure time E2(n) for P2(n) to the value given by the following equation.

$$(\lambda_2/\lambda_1) \cdot E2(n-1)$$

A synthesized image having a proper synthesis balance corresponding to the target value $\theta_T$ in response to the variation in the integration value A1 of the immediately preceding visible-spectrum image can thereby be obtained.

A case was described in which the visible-spectrum image was the first to be captured among the pair of the visible-spectrum image and the infrared-spectrum image that constitute a single synthesized image, but a configuration in which the infrared-spectrum image is captured first is also acceptable. The aforedescribed case in which $\lambda_1>1$ and $\lambda_2<1$ was also an example, and $\lambda_1$, $\lambda_2$ may have other values.

In the present imaging apparatus, the synthesized image is generated using the visible-spectrum image and the infrared-spectrum image, which are captured separately. Unlike an apparatus in which the visible-spectrum image and the infrared-spectrum image are captured simultaneously as a single image, the respective image signals of the visible-spectrum image and the infrared-spectrum image are obtained separately from the start, whereby, e.g., adjustment of the brightness of the infrared-spectrum image, color addition, and other processes are readily performed during synthesis. The configuration is such that the visible-spectrum image and the infrared-spectrum image are captured separately in a time-divided manner, whereby the respective imaging exposure times can be set separately. Advantages are thereby attained in that, e.g., the amount of exposure of the infrared-spectrum image can be ensured by lengthening the exposure time, the maximum amount of illumination of the excitation light source 22 can be set lower than in configurations in which the amount of exposure is ensured using only the illumination intensity of the excitation light source 22, and the size of the excitation light source 22 can be readily reduced.

An endoscopic imaging apparatus was described in the aforedescribed embodiment, but the present invention can also be applied to imaging apparatuses for other applications in which imaging is performed in an environment in which external light is essentially not present.

According to the present invention as described above, a visible-spectrum image and an infrared-spectrum image are captured in a time-divided manner using a single solid-state imaging device. Separate light sources are provided corresponding to the capture of the respective visible-spectrum image and infrared-spectrum image, and imaging is performed while emitting light in a band appropriate for each of the images. Separate exposure conditions can thereby be set for the capture of the respective visible-spectrum image and infrared-spectrum image, noise in the visible-spectrum image and the infrared-spectrum image can be minimized, and a proper synthesized image can be readily obtained.

What is claimed is:

1. An imaging apparatus, comprising:
a first light source for irradiating a subject with a first component light of a visible-spectrum band;
a second light source for irradiating the subject with a second component light of a wavelength for exciting a predetermined infrared-fluorescing substance for emitting infrared fluorescent light;
an optical filter for transmitting the infrared fluorescent light and a spectrum component corresponding to the first component light and for preventing the transmission of a band component corresponding to the second component light from among light from the subject;
a solid-state imaging device capable of capturing a visible-spectrum image and an infrared-spectrum image on the basis of light transmitted through the optical filter;
a control part for illuminating the first light source and the second light source in alternation and for causing the solid-state imaging device to capture an image when each of the first light source and the second light source is illuminated; and
an image signal-processing part for generating a synthesized image signal representing a synthesized image based on the visible-spectrum image captured as a result of the first light source being illuminated and on the infrared-spectrum image captured as a result of the second light source being illuminated,
wherein the control part sets exposure conditions during the capture of the visible-spectrum image and during the capture of the infrared-spectrum image, respectively, according to a desired synthesis balance of the visible-spectrum image and the infrared-spectrum image in the synthesized image,
wherein the control part
has a set first target signal level and second target signal level that are target signal levels for the visible-spectrum image and the infrared-spectrum image, respectively;
controls the exposure conditions of the visible-spectrum image using feedback control on the basis of deviation between the first target signal level and a signal level of the visible-spectrum image captured previously; and
controls the exposure conditions of the infrared-spectrum image using feedback control on the basis of deviation between the second target signal level and a signal level of the infrared-spectrum image captured previously.

2. An imaging apparatus, comprising:
a first light source for irradiating a subject with a first component light of a visible-spectrum band;
a second light source for irradiating the subject with a second component light of a wavelength for exciting a predetermined infrared-fluorescing substance for emitting infrared fluorescent light;
an optical filter for transmitting the infrared fluorescent light and a spectrum component corresponding to the first component light and for preventing the transmission of a band component corresponding to the second component light from among light from the subject;
a solid-state imaging device capable of capturing a visible-spectrum image and an infrared-spectrum image on the basis of light transmitted through the optical filter;
a control part for illuminating the first light source and the second light source in alternation and for causing the solid-state imaging device to capture an image when each of the first light source and the second light source is illuminated; and
an image signal-processing part for generating a synthesized image signal representing a synthesized image based on the visible-spectrum image captured as a result of the first light source being illuminated and on the infrared-spectrum image captured as a result of the second light source being illuminated,
wherein the control part sets exposure conditions during the capture of the visible-spectrum image and during the capture of the infrared-spectrum image, respectively, according to a desired synthesis balance of the visible-spectrum image and the infrared-spectrum image in the synthesized image; wherein
the signal-processing circuit synthesizes a pair of the visible-spectrum image and the infrared-spectrum image obtained continuously and generates the synthesized image; and
the control part
has a set target synthesis balance between a first image and a second image, in which an image captured first from among the pair of the visible-spectrum image and the infrared-spectrum image that are synthesized together is the first image, and an image captured later is the second image, and has a set first target signal level and second target signal level that are target signal levels for the first image and the second image, respectively, according to the target synthesis balance;
controls the exposure conditions of the first image using feedback control on the basis of deviation between the first target signal level and a signal level of the first image captured previously; and
controls the exposure conditions of the second image using a combination of feedback control on the basis of deviation between the second target signal level and a signal level of the second image captured previously, and feedforward control for implementing the target synthesis balance according to a signal level of the first image that was captured immediately beforehand.

* * * * *